US00PP22991P3

(12) United States Plant Patent
Zaiger et al.

(10) Patent No.: US PP22,991 P3
(45) Date of Patent: Aug. 28, 2012

(54) NECTARINE TREE NAMED 'SAUZEE PRINCE'

(50) Latin Name: ***Prunus persica* var. *nucipersica***
Varietal Denomination: Sauzee Prince

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 93 days.

(21) Appl. No.: 12/925,760

(22) Filed: Oct. 29, 2010

(65) Prior Publication Data

US 2012/0110709 P1 May 3, 2012

(51) Int. Cl.
*A01H 5/00* (2006.01)

(52) U.S. Cl. ..... Plt./188
(58) Field of Classification Search ..... Plt./188
See application file for complete search history.

*Primary Examiner* — Annette Para

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Heavy and regular production of fruit.
3. Early maturity of peento type fruit.
4. Firm with an attractive red blush.
5. Fruit with very good eating quality, mild, sweet, sub-acid flavor.
6. Fruit with firm white flesh, good handling and shipping quality.

1 Drawing Sheet

Botanical classification: *Prunus persica* var. *nucipersica*.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine trees, which are known to us, and mentioned herein, 'Sauzee King' Nectarine (U.S. Plant Pat. No. 16,258) and our proprietary seedling selections '7LR52' and '396LN381'.

STATEMENT REGARDING FEDERALLY SPONSORED RESEARCH AND DEVELOPMENT

Not applicable.

ORIGIN OF THE VARIETY

The new and distinct nectarine tree (*Prunus persica* var. *nucipersica*) was originated by us in our experimental orchard from seed of a first generation cross between the proprietary nectarine seedling '7LR52' and 'Sauzee King' Nectarine (U.S. Plant Pat. No. 16,258). The seed parent (7LR52) originated from an open pollinated selected proprietary nectarine seedling '396LN381'. We planted and grew a large number of these first generation seedlings, on their own root system and under close and careful observation we recognized the desirable tree growth and peento nectarine fruit characteristics of the present nectarine seedling and selected it for asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif. and shows that reproductions run true to the original tree and all characteristics of the tree and its fruit are established and transmitted through succeeding asexual propagations.

SUMMARY OF THE NEW VARIETY

The present new variety of nectarine tree is of large size, vigorous, upright growth and a productive and regular bearer of medium size, white, firm flesh fruit with very good flavor and eating quality. The fruit is further characterized by being peento shape, ripening in the early maturity season, and having an attractive red skin blush. In comparison to its seed parent (7LR52), the fruit of the new variety is peento shape compared to globose, is white flesh compared to yellow and is 10 days later in maturity. In comparison to its pollen parent 'Sauzee King' Nectarine (U.S. Plant Pat. No. 16,258) the fruit of the new variety is two weeks earlier in maturity and the tree requires approximately 400 hours less winter chilling.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of saucer nectarine tree, its flowers, foliage and fruit, as based on observations of 5 year old specimens grown near Modesto, Calif., with color in accordance with Munsell Book of Color.

Tree:

*Size.*—Large, pruned to 3 to 3.5 meters in height and width for economical harvesting of fruit. Varies with different cultural practices.

*Vigor.*—Vigorous, growth of 1.5 meters in height the first growing season. Varies with soil type, fertility and cultural practices.

*Form.*—Upright, usually pruned to vase shape.

*Branching habit.*—Upright, crotch angle approximately 35°, increases with crop load.

*Productivity.*—Productive, thinning and spacing of fruit necessary. Number of fruit set varies with climatic conditions during blooming period.

*Bearer.*—Regular, adequate fruit set 3 consecutive years. No alternate bearing observed.

*Fertility.*—Self-fertile.

*Density.*—Medium dense, usually pruned to vase shape by removing center branches and foliage which increases sunlight and air movement to the center of the tree.

*Hardiness.*—Hardy in all stone fruit growing areas in California. Tree grown in USDA Hardiness Zone 9. Winter chilling requirement approximately 350 hours at or below 45° F.

Trunk:

*Size.*—Large. Average circumference of 37.4 cm at 25.8 cm above ground on a 5 year old tree.

*Stocky.*—Medium stocky.

*Texture.*—Medium shaggy, becomes rougher with age.

*Color.*—Varies from 2.5Y 6/2 to 2.5Y 5/2.

Branches:

*Size.*—Medium. Average circumference 8.5 cm at 1.2 meters above ground. Crotch angle approximately 35°, increases with crop load.

*Surface texture.*—New growth is relatively smooth. Mature growth medium rough, roughness increases with age.

*Lenticels.*—Average number of 41 in a 25.8 sq cm section. Average length 3.9 mm. Average width 1.3 mm. Color 7.5YR 6/10.

*Color.*—New growth varies from 2.5GY 6/8 to 5GY 6/6 with 7.5R 3/6 where exposed to sunlight. Mature growth varies from 10YR 4/4 to 2.5Y 3/4, varies with age of growth.

Leaves:

*Size.*—Medium to large. Average length 137.1 mm. Average width 38.9 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentations over midrib and leaf veins. Lower surface relatively smooth except for small ridges created by midrib and pinnate venation. Both surfaces glabrous.

*Petiole.*—Average length 12.6 mm. Average width 1.7 mm. Longitudinally grooved. Surface glabrous. Color varies from 5GY 5/6 to 5GY 5/8.

*Glands.*—Type — reniform. Size — medium to large. Average length 1.6 mm. Average diameter 1.1 mm. Average number 4, varies from 2 to 6. Located primarily on the base of the leaf blade and the upper portion of the petiole. Color varies from 5GY 6/6 to 7.5R 4/12.

*Stipules.*—Average number at base of leaf blade — 2. Average length 8.0 mm. Margin — pectinate. Color varies from 2.5GY 6/8 to 2.5GY 5/8.

*Color.*—Upper surface varies from 7.5GY 2/4 to 5GY 3/6. Lower surface varies from 5GY 3/6 to 10GY 3/4. Midvein color varies from 2.5GY 8/2 to 5GY 8/4.

Flower buds:

*Size.*—Large. Average length 17.8 mm. Average diameter 11.4 mm.

*Hardiness.*—Hardy with respect to California winters.

*Form.*—Plump, conical becoming elongated before opening.

*Pedicel.*—Average length 4.5 mm. Average width 1.5 mm. Color varies from 5GY 7/6 to 5GY 6/6.

*Color.*—Varies from 7.5RP 6/12 to 5RP 7/6.

Flowers:

*Blooming period.*—Date of First Bloom Feb. 14, 2010. Date of Petal Fall Feb. 24, 2010, varies slightly with climatic conditions.

*Size.*—Large, showy. Average height 22.2 mm. Average diameter 49.5 mm.

*Petals.*—Normally 5, alternately arranged to the sepals. Form — ovate, narrows at point of attachment. Average length 23.5 mm. Average width 21.5 mm. Margin — sinuate. Color varies from 5RP 8/4 to 5RP 7/6. Both surfaces glabrous.

*Sepals.*—Normally 5, alternately arranged to the petals. Average length 7.7 mm. Average width 6.7 mm. Shape — ovate. Margin — entire. Surface — upper surface glabrous. Lower surface pubescent. Color — upper surface varies from 5GY 5/6 to 5GY 4/6. Lower surface varies from 2.5R 2/2 to 5R 3/2.

*Stamens.*—Average number 44. Average filament length 16.6 mm. Filament color varies from N9.5/(white) to 5RP 8/4. Anther color varies from 5R 3/10 to 7.5R 3/10.

*Pollen.*—Self-fertile. Color varies from 2.5Y 7/10 to 5Y 7/10.

*Pistil.*—Normally one. Surface — glabrous. Average length 19.0 mm. Stigma height approximately the same as the anthers. Color varies from 10Y 8/6 to 2.5GY 8/6.

*Fragrance.*—Slight.

*Color.*—Varies from 5RP 8/4 to 5RP 7/6.

*Number flowers per flower bud.*—Usually one.

*Pedicel.*—Average length 4.6 mm. Average width 1.8 mm. Color varies from 2.5GY 6/10 to 5GY 6/6.

Fruit:

*Maturity when described.*—Firm ripe.

*Date of first picking.*—Jun. 3, 2010.

*Date of last picking*.—Jun. 10, 2010, varies slightly with climatic conditions.

*Size*.—Medium. Average diameter axially 45.2 mm. Average transversely in suture plane 60.7 mm. Average weight 99.4 grams, varies slightly with fertility of the soil, amount of thinning and climatic conditions.

*Form*.—Peen-to shape.

*Suture*.—Distinct, extends from base to apex.

*Ventral surface*.—Lipped, well sealed.

*Apex*.—Retuse.

*Base*.—Retuse.

*Stem cavity*.—Rounded to slightly elongated in the suture plane. Average depth 2.5 mm. Average diameter 4.7 mm.

Stem:

*Size*.—Small. Average length 8.5 mm. Average diameter 3.2 mm.

*Color*.—Varies from 10Y 6/8 to 2.5GY 6/8.

Flesh:

*Ripens*.—Relatively even.

*Texture*.—Firm, meaty.

*Fibers*.—Few, small, tender.

*Firmness*.—Good flesh firmness.

*Aroma*.—Moderate.

*Amydgalin*.—Undetected.

*Eating quality*.—Very good.

*Flavor*.—Very good, sweet, low to sub-acid flesh.

*Juice*.—Moderate, enhances flavor.

*Brix*.—Average 14.8°, varies slightly with amount of fruit per tree and climatic conditions.

*Color*.—Varies between 7.5Y 8.5/2 to 10Y 8.5/2. Pit cavity color 10Y 9/2.

Skin:

*Thickness*.—Medium.

*Surface*.—Smooth.

*Pubescence*.—Wanting.

*Tendency to crack*.—Slight, primarily near the apex.

*Color*.—Ground color varies from 7.5Y 8/4 to 10Y 8/2. Overspread with 5R 4/8 to 5R 3/8.

*Tenacity*.—Tenacious to flesh.

*Astringency*.—None.

Stone:

*Type*.—Clingstone.

*Size*.—Medium. Average length 18.6 mm. Average width 27.2 mm. Average thickness 28.8 mm.

*Form*.—Peen-to shape, resembling shape of fruit.

*Base*.—Nearly flat.

*Apex*.—Nearly flat, only slightly rounded.

*Surface*.—Pitted throughout, pits vary from round to elongated.

*Sides*.—Unequal, one side extending further from the surface plane.

*Ridges*.—Small, narrow, ridges running from base toward apex.

*Tendency to split*.—None.

*Color*.—Varies from 10YR 8/6 to 2.5Y 8/6, when dry.

Kernel:

*Size*.—Medium. Average length 6.9 mm. Average width 8.9 mm. Average depth 7.6 mm.

*Form*.—Ovate, more rounded than most nectarine kernels.

*Taste*.—Bitter.

*Viability*.—Non-viable, incomplete embryo development.

*Skin*.—Varies from 7.5Y 9/2 to 10Y 9/2.

Use: Dessert.

*Market*.—Local and long distance.

Keeping quality: Good, held firm for 2 weeks at 38° to 42° F. without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree (*Prunus persica* var. *nucipersica*), substantially as illustrated and described.

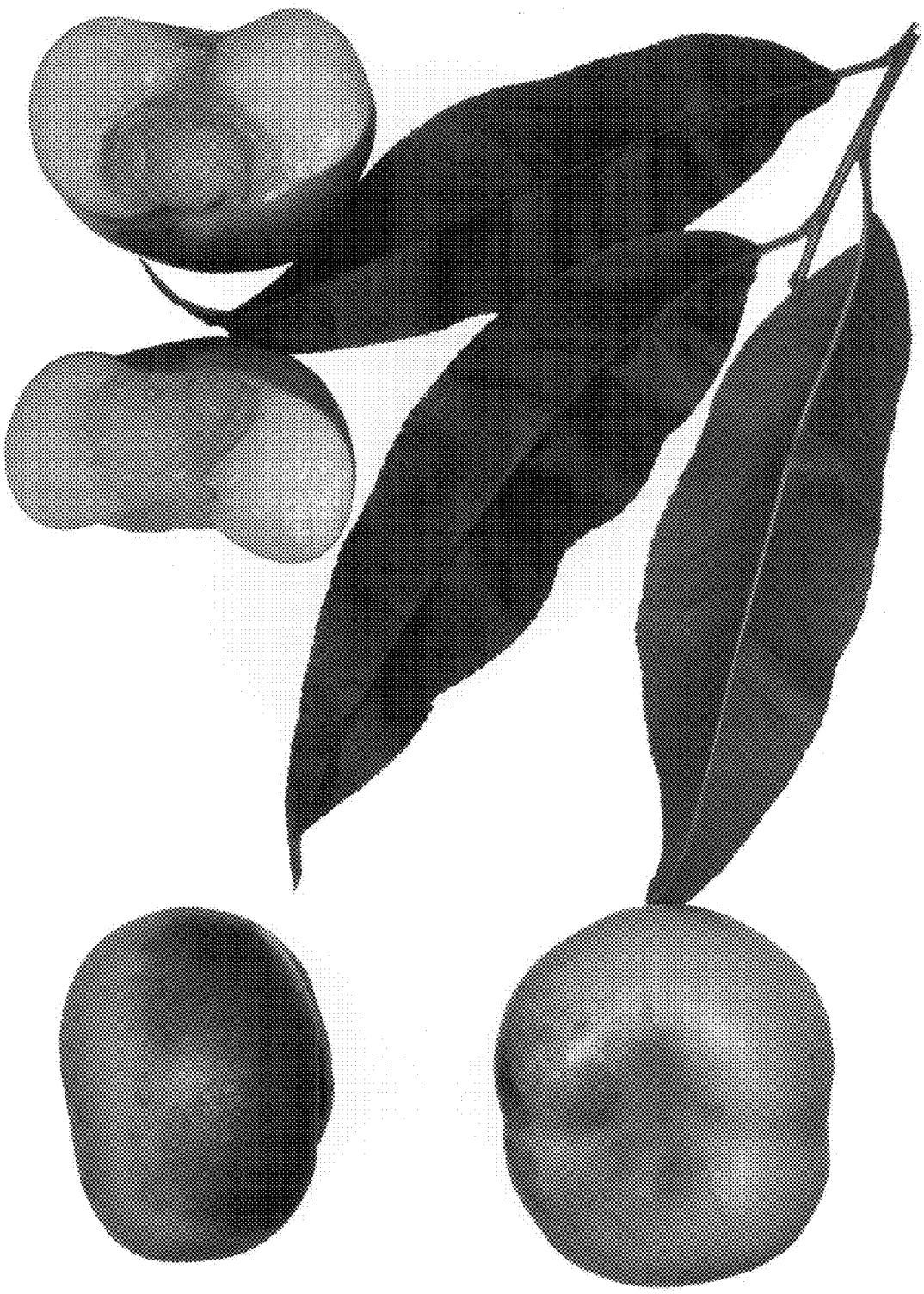

* * * * *